(12) United States Patent
Hodgkinson et al.

(10) Patent No.: US 9,572,576 B2
(45) Date of Patent: Feb. 21, 2017

(54) SURGICAL APPARATUS INCLUDING SURGICAL BUTTRESS

(71) Applicant: Covidien LP, Mansfield, MA (US)

(72) Inventors: Gerald Hodgkinson, Guilford, CT (US); Timothy D. Ebner, New Haven, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 819 days.

(21) Appl. No.: 13/924,804

(22) Filed: Jun. 24, 2013

(65) Prior Publication Data

US 2014/0021242 A1   Jan. 23, 2014

Related U.S. Application Data

(60) Provisional application No. 61/672,888, filed on Jul. 18, 2012.

(51) Int. Cl.
*A61B 17/072* (2006.01)

(52) U.S. Cl.
CPC ... *A61B 17/07207* (2013.01); *A61B 17/07292* (2013.01); *A61B 2017/07257* (2013.01); *F04C 2270/041* (2013.01); *Y10T 29/49826* (2015.01)

(58) Field of Classification Search
CPC .............. A61B 17/068; A61B 17/072; A61B 17/07207; A61B 17/07292; A61B 2017/07257
USPC .......................................... 227/175.1–182.1
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,079,696 A | 3/1963 | Bobrov |
| 3,124,136 A | 3/1964 | Usher |
| 3,490,675 A | 1/1970 | Green |
| 3,499,591 A | 3/1970 | Green |
| 4,347,847 A | 9/1982 | Usher |

(Continued)

FOREIGN PATENT DOCUMENTS

| | | |
|---|---|---|
| CA | 2 667 434 | 5/2008 |
| CN | 101310680 A | 11/2008 |

(Continued)

OTHER PUBLICATIONS

Extended European Search Report corresponding to EP 13 17 7437.4, completed Sep. 11, 2013 and mailed Sep. 19, 2013; (6 pp).

(Continued)

*Primary Examiner* — Stephen F Gerrity
*Assistant Examiner* — Joshua Kotis

(57) ABSTRACT

An end effector for a surgical stapling apparatus is provided which includes an anvil assembly and a surgical buttress. The anvil assembly includes an anvil body and an anvil plate. The anvil plate includes a bottom surface that defines a plurality of staple forming pockets. The anvil body and the anvil plate are selectively connectable. The surgical buttress includes a buttress body and a plurality of arms extending from the body. The arms are disposable between a top surface of the anvil plate and a bottom surface of the anvil body to support the buttress body against the bottom surface of the anvil plate when the anvil plate and the anvil body are connected to one another.

17 Claims, 4 Drawing Sheets

(56) References Cited

U.S. PATENT DOCUMENTS

| | | |
|---|---|---|
| 4,354,628 A | 10/1982 | Green |
| 4,429,695 A | 2/1984 | Green |
| 4,452,245 A | 6/1984 | Usher |
| 4,605,730 A | 8/1986 | Shalaby et al. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze |
| 5,205,459 A | 4/1993 | Brinkerhoff et al. |
| 5,263,629 A | 11/1993 | Trumbull et al. |
| 5,307,976 A | 5/1994 | Olson |
| 5,312,023 A | 5/1994 | Green |
| 5,314,471 A | 5/1994 | Brauker et al. |
| 5,318,221 A | 6/1994 | Green |
| 5,326,013 A | 7/1994 | Green |
| 5,332,142 A | 7/1994 | Robinson |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,865,361 A | 2/1999 | Milliman |
| 5,871,135 A | 2/1999 | Williamson IV et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,202,914 B1 | 3/2001 | Geiste |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 * | 12/2006 | Shelton, IV ...... A61B 17/07207 227/176.1 |
| 7,160,299 B2 | 1/2007 | Baily |
| 7,210,810 B1 | 5/2007 | Iversen et |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Bettuchi et al. |
| 7,722,642 B2 | 5/2010 | Williamson, IV |
| 7,744,627 B2 | 6/2010 | Orban, III et al. |
| 7,776,060 B2 | 8/2010 | Mooradian |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crows et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |

(56) References Cited

U.S. PATENT DOCUMENTS

| | | |
|---|---|---|
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,127,975 B2 | 3/2012 | Olson et al. |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,178,746 B2 | 5/2012 | Hildeberg et al. |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,869 B2 | 4/2013 | Heinrich |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,646,674 B2 | 2/2014 | Schulte et al. |
| 8,668,129 B2 | 3/2014 | Olson |
| 8,684,250 B2 | 4/2014 | Bettuchi |
| 8,721,703 B2 | 5/2014 | Fowler |
| 8,757,466 B2 | 6/2014 | Olson |
| 8,789,737 B2 | 7/2014 | Hodgkinson |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | (Prommersberger) Stopek et al. |
| 2002/0028243 A1 | 3/2002 | Masters |
| 2002/0091397 A1 | 7/2002 | Chen |
| 2002/0151911 A1 | 10/2002 | Gabbay |
| 2002/0165563 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0127131 A1* | 6/2005 | Mastri ............... A61B 17/0684 227/176.1 |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0085030 A1 | 4/2006 | Bettuchi et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |

(56) References Cited

U.S. PATENT DOCUMENTS

| | | |
|---|---|---|
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1* | 11/2008 | Bettuchi .......... A61B 17/07207 227/176.1 |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1* | 5/2009 | Tarinelli .......... A61B 17/07207 227/180.1 |
| 2009/0206125 A1 | 8/2009 | Huitema et al. |
| 2009/0206126 A1* | 8/2009 | Huitema .......... A61B 17/07207 227/175.1 |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1* | 9/2010 | Olson .......... A61B 17/07207 227/181.1 |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1* | 4/2011 | Ingmanson .......... A61B 17/072 227/176.1 |
| 2011/0215132 A1 | 9/2011 | Aranyi |
| 2011/0278347 A1 | 11/2011 | Olson et al. |
| 2012/0074199 A1 | 3/2012 | Olson |
| 2012/0080336 A1 | 4/2012 | Shelton |
| 2012/0083723 A1 | 4/2012 | Vitaris et al. |
| 2012/0145767 A1* | 6/2012 | Shah .......... A61B 17/07207 227/180.1 |
| 2012/0187179 A1 | 7/2012 | Gleiman |
| 2012/0197272 A1 | 8/2012 | Oray et al. |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0256380 A1 | 10/2013 | Schmid et al. |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |

(56) References Cited

U.S. PATENT DOCUMENTS

| | | |
|---|---|---|
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |

FOREIGN PATENT DOCUMENTS

| | | |
|---|---|---|
| CN | 101332110 A | 12/2008 |
| CN | 101626731 A | 1/2010 |
| DE | 1 99 24 311 | 11/2000 |
| EP | 0 594 148 | 4/1994 |
| EP | 0 327 022 | 4/1995 |
| EP | 0 667 119 | 8/1995 |
| EP | 1 064 883 | 1/2001 |
| EP | 1 256 317 | 11/2002 |
| EP | 1 256 318 | 11/2002 |
| EP | 1 520 525 | 4/2005 |
| EP | 1 621 141 | 2/2006 |
| EP | 1 702 570 | 9/2006 |
| EP | 1 759 640 | 3/2007 |
| EP | 1 815 804 | 8/2007 |
| EP | 1 825 820 | 8/2007 |
| EP | 1 929 958 | 6/2008 |
| EP | 1 994 890 | 11/2008 |
| EP | 2 005 894 | 12/2008 |
| EP | 2 005 895 | 12/2008 |
| EP | 2 008 595 | 12/2008 |
| EP | 2 039 308 A2 | 3/2009 |
| EP | 2 090 231 | 8/2009 |
| EP | 2 090 244 | 8/2009 |
| EP | 2 090 252 | 8/2009 |
| EP | 2 163 211 A2 | 3/2010 |
| EP | 2 189 121 A1 | 5/2010 |
| EP | 2 198 787 | 6/2010 |
| EP | 2 236 098 | 10/2010 |
| EP | 2 236 099 | 10/2010 |
| EP | 2 258 282 A2 | 12/2010 |
| EP | 2 292 276 A2 | 3/2011 |
| EP | 2 311 386 | 4/2011 |
| EP | 2 436 348 | 4/2012 |
| EP | 2 462 880 | 6/2012 |
| EP | 2 497 431 A1 | 9/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 762 091 A2 | 8/2014 |
| JP | 2000-166933 | 6/2000 |
| JP | 2002-202213 | 7/2002 |
| JP | 2007-124166 | 5/2007 |
| WO | WO 90/05489 | 5/1990 |
| WO | WO 95/16221 | 6/1995 |
| WO | WO 96/22055 | 7/1996 |
| WO | WO 97/01989 | 1/1997 |
| WO | WO 97/13463 | 4/1997 |
| WO | WO 98/17180 | 4/1998 |
| WO | 98/38923 A1 | 9/1998 |
| WO | WO 99/45849 | 9/1999 |
| WO | WO 03/082126 | 10/2003 |
| WO | WO 03/088845 | 10/2003 |
| WO | WO 03/094743 | 11/2003 |
| WO | WO 03/105698 | 12/2003 |
| WO | WO 2005/079675 | 9/2005 |
| WO | WO 2006/023578 | 3/2006 |
| WO | WO 2006/044490 | 4/2006 |
| WO | WO 2006/083748 | 8/2006 |
| WO | WO 2007/121579 | 11/2007 |
| WO | WO 2008/057281 | 5/2008 |
| WO | WO 2008/109125 | 9/2008 |
| WO | WO 2010/075298 | 7/2010 |
| WO | WO 2011/143183 | 11/2011 |
| WO | WO 2012/044848 | 4/2012 |

OTHER PUBLICATIONS

Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 08 72 6500.5, completed Feb. 20, 2014 and mailed Mar. 3, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).
European Search Report corresponding to EP 05 02 2585.3, completed Jan. 25, 2006 and mailed Feb. 3, 2006; 4 pages.
European Search Report corresponding to EP 06 00 4598, completed Jun. 22, 2006; 2 pages.
European Search Report corresponding to EP 06 01 6962.0, completed Jan. 3, 2007 and mailed Jan. 11, 2007; 10 pages.
International Search Report corresponding to International Application No. PCT/US2005/036740, completed Feb. 20, 2007 and mailed Mar. 23, 2007; 8 pages.
International Search Report corresponding to International Application No. PCT/US2007/022713, completed Apr. 21, 2008 and mailed May 15, 2008; 1 page.
International Search Report corresponding to International Application No. PCT/US2008/002981, completed Jun. 9, 2008 and mailed Jun. 26, 2008; 2 pages.
European Search Report corresponding to EP 08 25 1779, completed Jul. 14, 2008 and mailed Jul. 23, 2008; 5 pages.
European Search Report corresponding to EP 08 25 1989.3, completed Mar. 11, 2010 and mailed Mar. 24, 2010; 6 pages.
European Search Report corresponding to EP 10 25 0639.1, completed Jun. 17, 2010 and mailed Jun. 28, 2010; 7 pages.
European Search Report corresponding to EP 10 25 0715.9, completed Jun. 30, 2010 and mailed Jul. 20, 2010; 3 pages.
European Search Report corresponding to EP 05 80 4382.9, completed Oct. 5, 2010 and mailed Oct. 12, 2010; 3 pages.
European Search Report corresponding to EP 10 25 1437.9, completed Nov. 22, 2010 and mailed Dec. 16, 2010; 3 pages.

(56) References Cited

OTHER PUBLICATIONS

European Search Report corresponding to EP 09 25 2897.5, completed Feb. 7, 2011 and mailed Feb. 15, 2011; 3 pages.
European Search Report corresponding to EP 10 25 0642.5, completed Mar. 25, 2011 and mailed Apr. 4, 2011; 4 pages.
European Search Report corresponding to EP 11 18 8309.6, completed Dec. 15, 2011 and mailed Jan. 12, 2012; 3 pages.
European Search Report corresponding to EP 12 15 2229.6, completed Feb. 23, 2012 and mailed Mar. 1, 2012; 4 pages.
European Search Report corresponding to EP 12 15 0511.9, completed Apr. 16, 2012 and mailed Apr. 24, 2012; 7 pages.
European Search Report corresponding to EP 12 15 2541.4, completed Apr. 23, 2012 and mailed May 3, 2012; 10 pages.
European Search Report corresponding to EP 12 16 5609.4, completed Jul. 5, 2012 and mailed Jul. 13, 2012; 8 pages.
European Search Report corresponding to EP 12 15 8861.0, completed Jul. 17, 2012 and mailed Jul. 24, 2012; 9 pages.
European Search Report corresponding to EP 12 16 5878.5, completed Jul. 24, 2012 and mailed Aug. 6, 2012; 8 pages.
Extended European Search Report corresponding to EP 12 19 1035.0, completed Jan. 11, 2013 and mailed Jan. 18, 2013; 7 pages.
Extended European Search Report corresponding to EP 12 18 6175.1, completed Jan. 15, 2013 and mailed Jan. 23, 2013; 7 pages.
Extended European Search Report corresponding to EP 12 19 1114.3, completed Jan. 23, 2013 and mailed Jan. 31, 2013; 10 pages.
Extended European Search Report corresponding to EP 12 19 2224.9, completed Mar. 14, 2013 and mailed Mar. 26, 2013; 8 pages.
Extended European Search Report corresponding to EP 12 19 6904.2, completed Mar. 28, 2013 and mailed Jul. 26, 2013; 8 pages.
Extended European Search Report corresponding to EP 12 19 6911.7, completed Apr. 18, 2013 and mailed Apr. 24, 2013; 8 pages.
Extended European Search Report corresponding to EP 07 00 5842.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 12 19 8749.9, completed May 21, 2013 and mailed May 31, 2013; 8 pages.
Extended European Search Report corresponding to EP 13 15 6297.7, completed Jun. 4, 2013 and mailed Jun. 13, 20131; 7 pages.
Extended European Search Report corresponding to EP 13 17 3985.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.

Extended European Search Report corresponding to EP 13 17 6895.4, completed Nov. 29, 2013 and mailed Dec. 12, 2013; 5 pages.
European Examination Report issued in corresponding EP Application No. 13176895.4 dated Nov. 12, 2015.
Chinese First Office Acton for CN 2013103036903 dated Jun. 30, 2016.
Chinese Notification of Reexamination corresponding to counterpart Int'l Appln. No. CN 201010517292.8 dated Jun. 2, 2015.
Extended European Search Report corresponding to counterpart Int'l Appln. No. EP 14 15 2060.1 dated Aug. 14, 2015.
Japanese Office Action corresponding to counterpart Int'l Appln. No. JP 2014-216989 mailed Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 mailed Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 mailed Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019A dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 mailed May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).

(56) References Cited

OTHER PUBLICATIONS

Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).

* cited by examiner

SURGICAL APPARATUS INCLUDING SURGICAL BUTTRESS

CROSS-REFERENCE TO RELATED APPLICATIONS

This application claims the benefit of and priority to U.S. Provisional Patent Application No. 61/672,888, filed Jul. 18, 2013, the entire disclosure of which is incorporated by reference here.

BACKGROUND

Technical Field

This application relates to a surgical apparatus, and more particularly, to a surgical buttress for use with a surgical stapling apparatus during operation of the stapling apparatus to apply a plurality of surgical staples to body tissue.

Background of Related Art

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

Although the present disclosure includes, but is not limited to use with endoscopic surgery, endoscopic surgery is one of the truly great advances in recent years to reduce the invasiveness of surgical procedures. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

In many surgical procedures, including those involved in open and endoscopic surgery, it is often necessary to staple tissue. It is especially challenging during endoscopic surgery because of the small openings through which the stapling of tissues must be accomplished. Instruments for this purpose can include two elongated members which are respectively used to capture or clamp tissue. Surgical devices wherein tissue is first grasped or clamped between opposing jaw structure and then joined by surgical fasteners are well known in the art. Typically, one of the members carries a fastener cartridge which houses a plurality of staples arranged in at least two lateral rows while the other member has an anvil that defines a surface for forming the staple legs as the staples are driven from the staple cartridge. The fasteners are typically in the form of surgical staples but two part polymeric fasteners can also be utilized. Generally, the stapling operation is effected by cam bars or wedges that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. U.S. Surgical, the assignee of the present application, has manufactured and marketed endoscopic stapling instruments for several years. Examples of such instruments include the Multifire ENDO GIA™ 30 and Multifire ENDO GIA™ 60 instruments. Other examples of such staplers are disclosed in U.S. Pat. Nos. 4,429,695 and 5,065,929.

In staplers of the general type described above, surgical buttress material may be used in combination with these instruments as reinforcement to staple lines to further promote proper staple formation while reducing twisting/malformation caused by any misalignment or unusual or non-uniform tissue. These instruments have provided significant clinical benefits. Nonetheless, improvements are possible, for example, by reducing the complexity of manufacture and/or application.

SUMMARY

According to one aspect, the present disclosure relates to an end effector for a surgical stapling apparatus. The end effector includes an anvil assembly and a surgical buttress. The anvil assembly includes an anvil body and an anvil plate that are selectively connectable. The anvil plate includes a bottom surface that defines a plurality of staple forming pockets. The surgical buttress includes a buttress body and a plurality of arms extending from the body. The surgical buttress may be formed of a non-woven material and may be made from a material selected from the group comprising polyglytone 6211, glycolide, caprolactone, trimethylene carbonate, lactide and combinations thereof.

The arms of the surgical buttress may extend from side edges of the buttress body and may be integrally formed with the buttress body. Notably, the arms of the surgical buttress may be foldable over one or both of a top and a bottom surface of the buttress body. As can be appreciated, the arms are disposable between a top surface of the anvil plate and a bottom surface of the anvil body to support the buttress body against the bottom surface of the anvil plate when the anvil plate and the anvil body are connected to one another. The anvil body defines one or more channels in a bottom surface of the anvil body for the reception of one or more of the arms of the surgical buttress.

According to one aspect, a surgical stapling apparatus includes a first jaw assembly, a second jaw assembly, a plurality of fasteners, and a surgical buttress. The first jaw assembly includes an anvil body and an anvil plate. The anvil plate defines a plurality of fastener forming pockets in a bottom surface thereof. The second jaw assembly includes a fastener cartridge defining a plurality of fastener retaining slots. The plurality of fasteners is disposed within the fastener slots and configured and dimensioned to be formed by the fastener pockets of the anvil plate upon a firing of the stapling apparatus. The surgical buttress includes a buttress body and a plurality of arms extending from the buttress body. As appreciated, the surgical buttress may be formed of a non-woven material and may be made from a material selected from the group comprising polyglytone 6211, glycolide, caprolactone, trimethylene carbonate, lactide and combinations thereof.

The arms of the surgical buttress may be integrally formed with the buttress body and may extend from side surfaces of the buttress body. The arms may be foldable over one or both of a top and a bottom surface of the buttress body. The arms may be disposed between a top surface of the anvil plate and a bottom surface of the anvil body to support the buttress body against the bottom surface of the anvil plate. The anvil body of the first jaw assembly may define one or more channels in the bottom surface thereof for the reception of one or more of the arms of the surgical buttress. The one or more arms may be released from the one or more channels upon a firing of the stapling apparatus.

The surgical stapling apparatus may include a knife assembly including a knife that is movable through one or both of the first and second jaw assemblies to cut one or both of the buttress body and the arms of the surgical buttress to facilitate a release of at least the buttress body from against the bottom surface of the anvil plate.

According to yet another aspect, a method of mounting a surgical buttress to an end effector of a surgical stapling apparatus includes providing an end effector for a surgical stapling apparatus. The end effector includes a first jaw assembly and a second jaw assembly. The first jaw assembly includes an anvil body and an anvil plate. The anvil plate defines a plurality of fastener forming pockets in a bottom surface thereof. The second jaw assembly includes a cartridge defining a plurality of fastener retaining slots for retaining a plurality of fasteners that are formed by the fastener forming pockets upon a firing of the stapling apparatus. The method involves providing a surgical buttress including a buttress body and a plurality of arms extending from the body and mounting the arms of the surgical buttress between a top surface of the anvil plate and the bottom surface of the jaw so that the buttress body is disposed adjacent the bottom surface of the anvil plate.

The method may include the step of positioning the arms of the surgical buttress within channels defined in the bottom surface of the anvil plate. One step may include forming the surgical buttress from a non-woven material. The method may involve forming the surgical buttress from a material selected from the group comprising polyglytone 6211, glycolide, caprolactone, trimethylene carbonate, lactide and combinations thereof.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Figure 1:
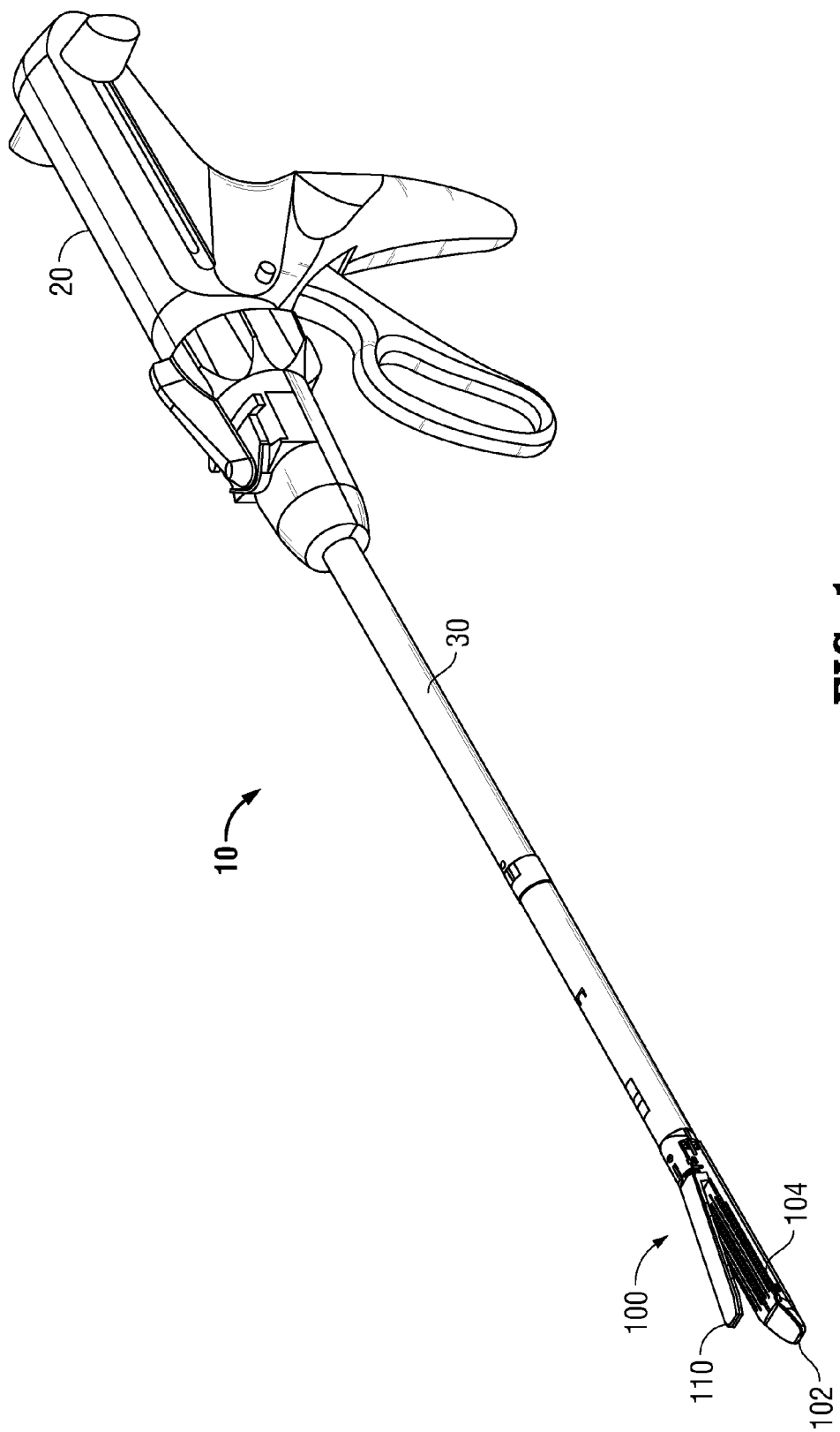
FIG. 1 is a perspective view of one embodiment of an endoscopic surgical stapling apparatus in accordance with the present disclosure.

As used herein, the term "clinician" refers to a doctor, a nurse, or any other care provider and may include support personnel. Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the clinician and the term "distal" refers to the end of the apparatus that is farther from the clinician. In the following description, well-known functions or constructions are not described in detail to avoid obscuring the present disclosure in unnecessary detail.

In general, linear staplers, including open and endoscopic devices, can have two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such an instrument is disclosed, for example, in U.S. Pat. No. 6,202,914, the entire content of which is incorporated herein by reference.

Some staplers apply a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. An example of such a stapler is disclosed in U.S. Pat. No. 5,065,929, the entire content of which is incorporated herein by reference.

Some of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,865,361, the entire content of which is incorporated herein by reference.

Referring now to the drawings, in which like reference numerals identify identical or substantially similar parts throughout the several views, FIG. 1 illustrates a surgical stapling apparatus 10 that may be arranged for use with minimally invasive (i.e., endoscopic, laparoscopic, etc.) or open stapling procedures. The surgical stapling apparatus 10 includes a housing 20 and an elongate member 30 that extends distally from the housing 20. A distal end of the elongate member 30 supports a proximal end of an end effector 100 that defines a longitudinal axis "L" between proximal and distal ends of the end effector 100. The end effector 100 includes first jaw member or cartridge assembly 102 that is configured to selectively receive a staple cartridge 104 and second jaw member or anvil assembly 110. The cartridge assembly 102 may be a single use loading unit. Indeed, the staple cartridge 104 houses staples and/or other surgical fasteners other than staples. The cartridge assembly 102 and/or the staple cartridge 104 may be selectively replaceable, either individually or collectively.

Figure 2:
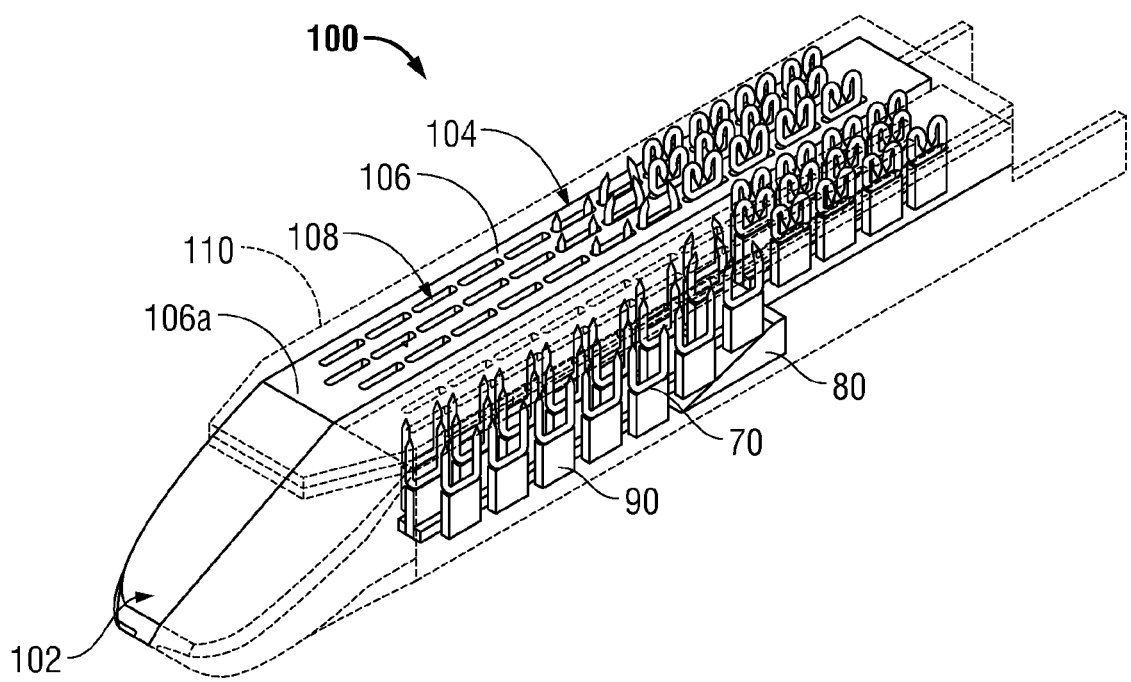
FIG. 2 is an enlarged perspective view illustrating an end effector of the presently disclosed surgical stapling apparatus during a fastener applying operation as fasteners are being sequentially fired.
Figure 6:
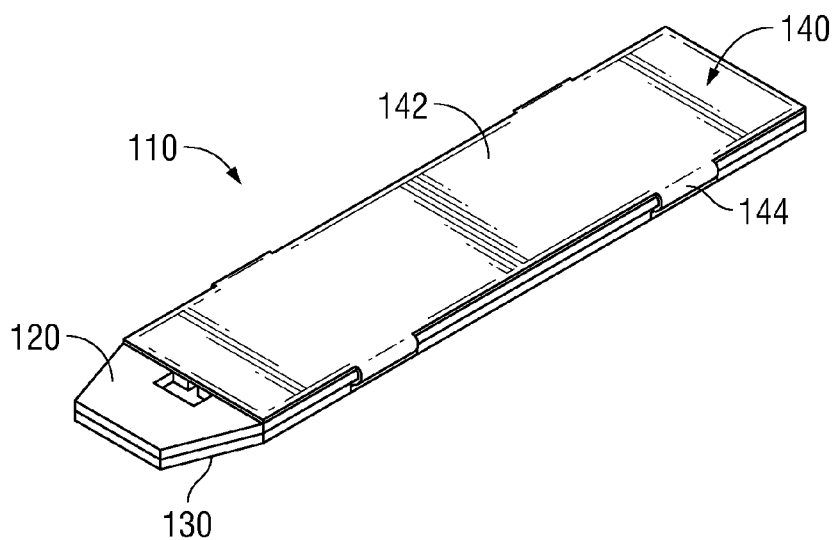
FIG. 6 is a bottom perspective view, with parts assembled, of the anvil assembly shown in FIG. 5.

With reference to FIG. 2, the staple cartridge 104 of the cartridge assembly 102 includes a cartridge housing 106 including a tissue contacting surface 106a having a plurality of rows of staple retaining slots (also referred to herein as stapler slots and fastener slots) 108 formed therein that house a plurality of fasteners or staples 70. With reference to FIGS. 2 and 6, the plurality of staples 70 may be sequentially formed in fastener forming pockets 124 defined in a tissue contacting surface 120b of the anvil assembly 110 upon a distal advancement of a cam bar and/or a sled 80 into a plurality of staple pusher members 90 as will be described in greater detail below.

Figure 3:
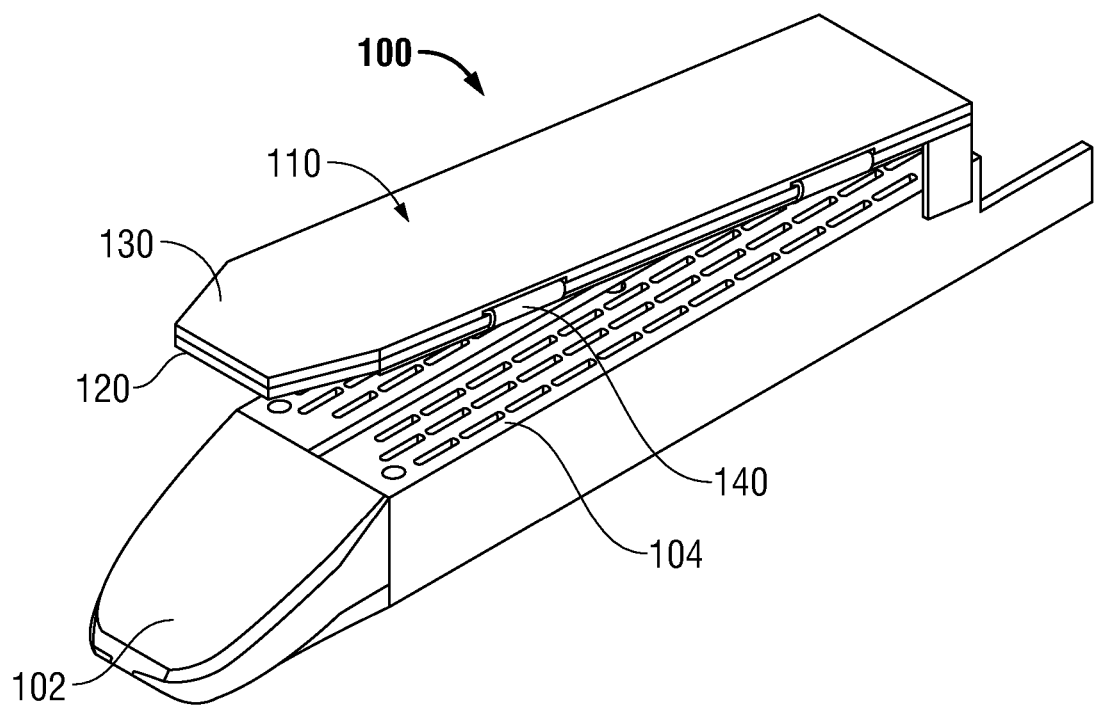
FIG. 3 is another perspective view of the end effector with a surgical buttress secured to an anvil assembly thereof.

Referring now to FIG. 3, anvil assembly 110 of the end effector 100 includes an anvil plate 120, an anvil body 130, and a surgical buttress 140 (as used herein, "surgical buttress" includes a pledget, gasket, buttress, or staple line reinforcement structure). The anvil assembly 110, or portions thereof, may be disposable or reusable.

Figure 4:
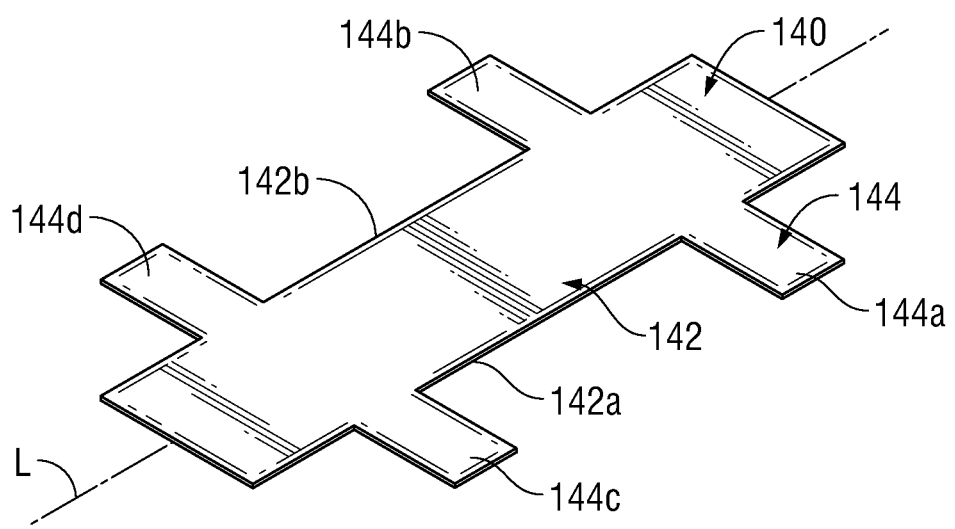
FIG. 4 is a perspective view of the surgical buttress shown in FIG. 3.

As depicted in FIG. 4, the surgical buttress 140 includes a body 142, having a substantially rectangular shape, and a plurality of arms 144. The body 142 and the plurality of arms 144 may be integrally formed or separately attachable. In particular, the surgical buttress 140 includes a first arm 144a and a second arm 144b which extend laterally from opposed side edges or surfaces 142a, 144b of body 142 at a proximal region of body 142. A third arm 144c and a fourth arm 144d extend laterally from opposed side surfaces 142a, 142b of body 142 at a distal region of body 142. Of course, any number of arms 144 may be disposed anywhere along the side surfaces 142a, 142b of body 142.

One or more of the arms 144 may be disposed transverse or substantially transverse (i.e., non-orthogonal) to a longitudinal axis "L" that extends through the body 142 between the proximal and distal ends of the body 142. As can be appreciated, one more of the arms 144 may be disposed at any suitable angle relative to the longitudinal axis of the body 142 and may extend to any suitable distance from the side surfaces 142a, 142b of the body 142. Indeed, one or more of the arms 144 may have any suitable length, width and/or thickness. Any number of the arms 144 may be offset from, and/or aligned with, any number of the other arms 144.

In embodiments, the surgical buttress 140, or portions thereof, may be made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, the surgical buttress 110, or portions thereof, may be made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes. In embodiments, the surgical buttress 140, or portions thereof, may be a non-woven material selected from the group including polyglytone 6211, glycolide, caprolactone, trimethylene carbonate, lactide and combinations thereof.

Figure 5:
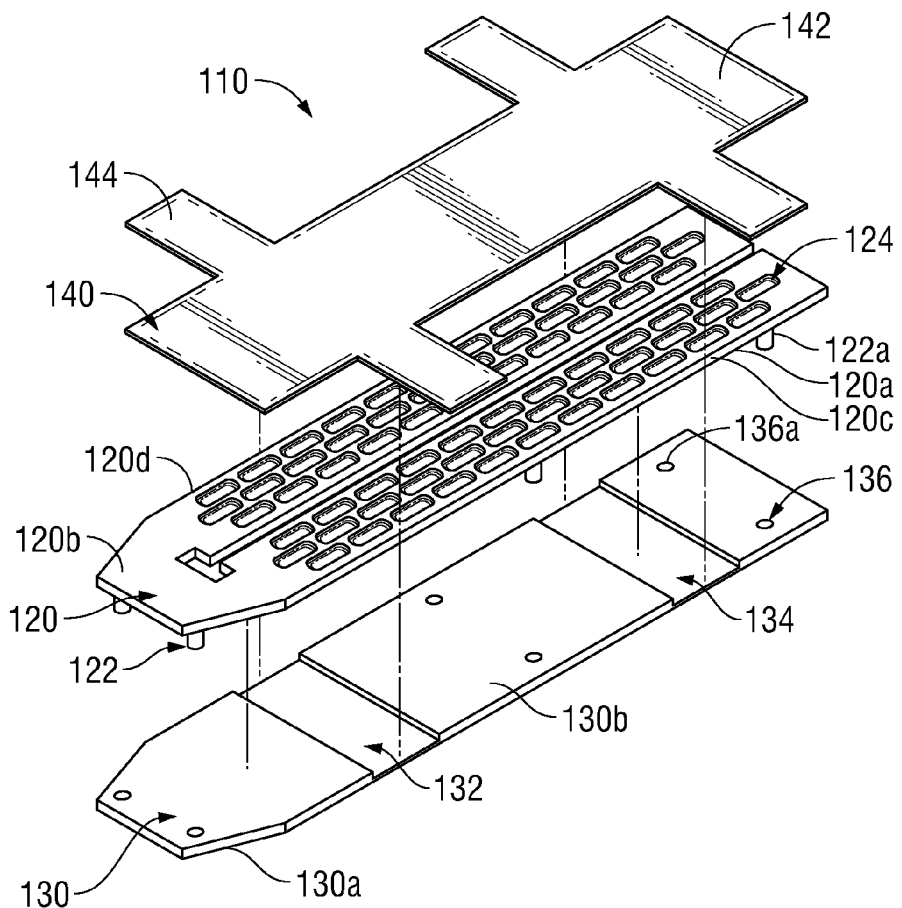
FIG. 5 is a bottom perspective view, with parts separated, of the anvil assembly of the end effector shown in FIG. 3.

Turning now to FIGS. 5-6, the anvil body 130 defines a first transverse channel 132 and a second transverse channel 134 therethrough that align with one or more of the arms 144 of the surgical buttress 140 when the surgical buttress 140 is properly aligned with the anvil body 130. The first and second channels 132, 134 are dimensioned to receive one or more arms 144 of the surgical buttress 140 to support the arms 144 of the surgical buttress 140 between the anvil body 130 and the anvil plate 120 while maintaining the body 142 of the surgical buttress 140 positioned adjacent to a bottom or tissue contacting surface 120b of the anvil plate 120. In particular, the first and second channels 132, 134 are recessed from a bottom surface 130b of the anvil body 130 and are disposed in a longitudinally spaced apart relationship along the anvil body 130.

Anvil body 130 may include an anvil body securement feature 136 that mates with an anvil plate securement feature 122 to secure the anvil body 130 and the anvil plate 120 together when engaged. As can be appreciated, the one or more securement features may include any suitable mechanical or chemical feature. For example, as illustrated in FIG. 6, a pin 122a may extend from a top surface 120a of anvil plate 120 to engage with an aperture 136a defined within anvil body 130. Other mechanical arrangements may include hook-and-loop fasteners, friction-fit engagement, and/or snap-fit engagement In embodiments, an adhesive and/or a magnetic material may be included on any suitable surface of the anvil body 130 and/or anvil plate 120 to facilitate securement of the anvil body 130 and the anvil plate 120.

Notably, surgical buttress 140, or portions thereof, may be operably connected to the anvil assembly 110, or portions thereof, via any suitable chemical or mechanical feature (e.g., adhesive, magnet, hook-and-loop, snap-fit, straps, threads, welding, etc.).

To assemble, the surgical buttress 140 is positioned adjacent the anvil plate 120 such that the body 142 of the surgical buttress 140 is disposed against/adjacent the bottom surface 120b of the anvil plate 120, and such that the arms 144 of the surgical buttress 140 are folded around side surfaces 120c, 120d of the anvil plate 120 to position the arms 144 along the top surface 120a of the anvil plate 120. In this regard, the anvil plate 120 may be secured to the anvil body 130 via the securement features 122, 136 so that the arms 144 of the surgical buttress are disposed within the channels 132, 134 between the bottom surface 130b of the anvil body 130 and the top surface 120a of the anvil plate 120. Suitably, the anvil plate 120 may be secured to the anvil body 130 prior to the attachment of the surgical buttress 140. In this regard, the surgical buttress 140 is positioned adjacent to the anvil plate 120 so that the arms 144 of the surgical buttress 140 may be inserted within the channels 132, 134 to mount the body 142 of the surgical buttress 140 adjacent to the bottom surface 120b of anvil plate 120 so that the body 142 of the surgical buttress 140 is disposed in contact with the bottom surface 120b of the anvil plate 120.

Referring again to FIGS. 5-6, upon proper attachment to the anvil plate 120 and/or the anvil body 130, the body 142 of the surgical buttress 140 may extend between proximal and distal portions of the anvil plate 120. In particular, the body 142 of the surgical buttress 140 may substantially overlie some or all of the fastener forming pockets 124 (FIG. 6) defined in the anvil plate 120.

After clamping the first and second jaw members 102, 110 of the surgical stapling apparatus 10 against tissue of a patient, the surgical stapling apparatus 10 may then be fired to deploy the fasteners 70 through the fastener slots 108 of the staple cartridge 104. Upon firing, the fasteners 70 pass through the fastener slots 108 and the legs of the fasteners 70 penetrate through the tissue clamped by the jaw members 102, 110 and the body 142 of the surgical buttress 140. The fasteners 70 are then formed against the fastener forming pockets 124 of the anvil plate 120, thereby affixing the body 142 of the surgical buttress 140 to the clamped tissue. Concomitantly therewith, a knife (not shown) translatably disposed within the end effector 100 cuts through the tissue clamped between the jaw members 102, 110, through at least a portion of the body 142 of the surgical buttress 140. In certain embodiments, the knife can be configured and arranged to cut through the body 142 prior to firing.

The surgical buttress 140 disengages from the cartridge housing 106 of the staple cartridge 104 so that the body 142 and/or the arms 144 of the surgical buttress 140 may remain attached to the tissue via the fasteners 70. Alternatively, the arms 144 and/or body 142 of the surgical buttress 140 can be cut with shears, or can include perforations or frangible features for separating any suitable portion of the surgical buttress 140 (i.e., arms 144) from other portions of the surgical buttress 140 (i.e., body 142).

If further application or use of a surgical buttress is necessary, a new surgical buttress 140 may be mounted onto the anvil assembly 110, as described above. The user may then repeat a fastening process. It is further contemplated that, if desired, a clinician may remove surgical buttress 140 from anvil assembly 110 prior to a use of surgical stapling apparatus 10.

Alternatively or additionally, any suitable surgical buttress may be positioned on cartridge assembly 102 before or after firing as can be appreciated.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. An end effector for a surgical stapling apparatus, comprising:
    an anvil assembly including an anvil body and an anvil plate, the anvil plate including a bottom surface defining a plurality of staple forming pockets, the anvil body and the anvil plate being selectively connectable;
    a surgical buttress including a buttress body and a plurality of arms extending from the body, the arms being disposable between a top surface of the anvil plate and a bottom surface of the anvil body such that the top surface of the anvil plate and the bottom surface of the anvil body contact the arms to support the buttress body against the bottom surface of the anvil plate when the anvil plate and the anvil body are connected to one another;
    wherein the arms of the surgical buttress extend from side edges of the buttress body; and
    wherein the arms are foldable over an outer side surface of the anvil plate to facilitate securement of the arms between the top surface of the anvil plate and the bottom surface of the anvil body.

2. The end effector of claim 1, wherein the anvil body defines at least one channel in a bottom surface of the anvil body for the reception of at least one of the arms of the surgical buttress.

3. The end effector of claim 2, wherein the surgical buttress is formed of a non-woven material.

4. The end effector of claim 2, wherein the surgical buttress is made from a material selected from the group comprising polyglytone 6211, glycolide, caprolactone, trimethylene carbonate, lactide and combinations thereof.

5. The end effector of claim 1, wherein the arms of the surgical buttress are integrally formed with the buttress body.

6. A surgical stapling apparatus, comprising:
    a first jaw assembly including an anvil body and an anvil plate, the anvil plate defining a plurality of fastener forming pockets in a bottom surface thereof;
    a second jaw assembly including a fastener cartridge defining a plurality of fastener retaining slots;
    a plurality of fasteners disposed within the fastener slots and configured and dimensioned to be formed by the fastener pockets of the anvil plate upon a firing of the stapling apparatus;
    a surgical buttress including a buttress body and a plurality of arms extending from the buttress body, the arms being disposed between, and secured by, a top surface of the anvil plate and a bottom surface of the anvil body to support the buttress body against the bottom surface of the anvil plate;
    wherein the arms of the surgical buttress extend from side edges of the buttress body; and
    wherein the arms are foldable over an outer side surface of the anvil plate.

7. The surgical stapling apparatus of claim 6, wherein the anvil body defines at least one channel in the bottom surface thereof for the reception of at least one of the arms of the surgical buttress.

8. The surgical stapling apparatus of claim 7, wherein the at least one arm is released from the at least one channel upon a firing of the stapling apparatus.

9. The surgical stapling apparatus of claim 6, wherein the surgical buttress is formed of a non-woven material.

10. The surgical stapling apparatus of claim 6, wherein the surgical buttress is made from a material selected from the group comprising polyglytone 6211, glycolide, caprolactone, trimethylene carbonate, lactide and combinations thereof.

11. The surgical stapling apparatus of claim 6, further comprising a knife assembly including a knife that is movable through at least one of the first and second jaw assemblies to cut at least one of the buttress body and the arms of the surgical buttress to facilitate a release of at least the buttress body from against the bottom surface of the anvil plate.

12. The surgical stapling apparatus of claim 6, wherein the arms of the surgical buttress are integrally formed with the buttress body.

13. The surgical stapling apparatus of claim 6, wherein at least one of the arms is receivable in a channel defined between the anvil body and the anvil plate, the channel opening laterally through an outer surface of the anvil body.

14. A method of mounting a surgical buttress to an end effector of a surgical stapling apparatus, the method comprising:

providing an end effector for a surgical stapling apparatus, the end effector including a first jaw assembly and a second jaw assembly, the first jaw assembly including an anvil body and an anvil plate, the anvil plate defining a plurality of fastener forming pockets in a bottom surface thereof, the second jaw assembly including a cartridge defining a plurality of fastener retaining slots for retaining a plurality of fasteners that are formed by the fastener forming pockets upon a firing of the stapling apparatus;

providing a surgical buttress including a buttress body and a plurality of arms extending from the buttress body;

folding the arms around an outer side surface of the anvil plate to tuck the arms of the surgical buttress between a top surface of the anvil plate and the bottom surface of the anvil body so that the buttress body is disposed adjacent the bottom surface of the anvil plate.

15. The method of claim 14, further comprising securing the arms of the surgical buttress within channels defined in the bottom surface of the anvil body, the channels opening laterally through a side surface of the anvil body.

16. The method of claim 14, further comprising forming the surgical buttress from a non-woven material.

17. The method of claim 16, further comprising forming the surgical buttress from a material selected from the group comprising polyglytone 6211, glycolide, caprolactone, trimethylene carbonate, lactide and combinations thereof.

* * * * *